United States Patent [19]

Kim

[11] 3,939,262
[45] Feb. 17, 1976

[54] DENTIFRICES
[75] Inventor: Keun Y. Kim, Chesterfield, Mo.
[73] Assignee: Monsanto Company, St. Louis, Mo.
[22] Filed: Jan. 21, 1974
[21] Appl. No.: 435,052

[52] U.S. Cl. .................................. 424/52; 424/49
[51] Int. Cl.² .......................................... A61K 7/18
[58] Field of Search ............................ 424/49–58

[56] References Cited
UNITED STATES PATENTS

| | | | |
|---|---|---|---|
| 3,538,230 | 11/1970 | Pader et al. | 424/50 |
| 3,840,657 | 10/1974 | Norfleet | 424/49 |
| 3,842,167 | 10/1974 | Block et al. | 424/49 |

*Primary Examiner*—Shep K. Rose
*Attorney, Agent, or Firm*—N. E. Willis; H. B. Roberts; T. N. Wallin

[57] ABSTRACT

Dental creams, particularly translucent dental creams, containing finely divided synthetic amorphous silica polishing agents, such polishing agents have an average refractive index of from about 1.410 to 1.440.

6 Claims, No Drawings

DENTIFRICES

BACKGROUND OF THE INVENTION

1. Field of the Invention

This invention relates to dentifrice compositions containing finely divided synthetic amorphous silica polishing agents. More particularly, it relates to either translucent or opaque dental creams.

2. DESCRIPTION OF THE PRIOR ART

Commercially available silica xerogels are currently used as the polishing agent in translucent dental creams. These creams are translucent because the 1.46 refractive index of the solid phase, which is essentially a silica xerogel, matches that of the liquid phase, which is essentially a humectant and water.

In preparing them, the humectant concentration in the liquid phase is adjusted so the refractive index of this phase matches that of the solid phase. These silica xerogels require high concentrations of humectant, for example 70% sorbitol or 90% glycerin. Additionally, they are difficult to prepare because of the gelatinous nature of the crude gel.

Dental creams containing readily prepared silica polishing agents that do not require high humectant concentrations to give translucent creams would be an advancement in the art.

BRIEF DESCRIPTION OF THE INVENTION

In accordance with this invention, translucent dental creams containing synthetic amorphous silica polishing agents are provided containing lower humectant concentrations. These creams comprise:

1. a solid phase comprising as the polishing agent in a polishing amount, a synthetic amorphous silica, said polishing agent having an average refractive index of from about 1.410 to 1.440, and
2. a liquid phase comprising water and a humectant, with the refractive index of said liquid phase being essentially identical to the refractive index of said solid phase.

When these silica polishing agents are used to prepare translucent dental creams, the concentration of sorbitol or glycerin can be considerably reduced, i.e., to a 47 to 60% level, due to the low refractive indices of these polishing agents. Additionally, these silicas provide good polishing as well as cleaning when applied to the teeth in the conventional manner and they do not excessively scratch or abrade the teeth. In addition, they are compatible with most common dentifrice ingredients.

Another aspect of this invention relates to opaque dentifrice compositions containing the above-mentioned silica polishing agents, particularly opaque dental creams.

DETAILED DESCRIPTION OF THE INVENTION

As mentioned, synthetic amorphous silicas are used as the polishing agents in the dentifrice compositions of this invention. Individual silica particles have a refractive index (RI) of from about 1.410 to 1.440.

These silicas are prepared from particulate hydrous alkali metal silicates. It is critical that the alkali metal silicates be particulate and that they contain 10 to 25%, preferably 15 to 20% by weight of water.

These silicates have an $SiO_2/M_2O$ ratio of from about 1.6 to about 3.75, preferably 2.0 to about 3.2. They may be prepared by dehydrating alkali metal silicate solutions by any known drying method such as spray-drying, drum-drying, and high pressure extrusion, as described in U.S. Pat. No. 3,450,494. As the result of dehydration, the alkali metal silicate ions are relatively fixed in position. In the case of spray-dried silicates, they are fixed in the spherical beads.

Because it is readily available, it is preferred to use sodium silicate, particularly spray-dried sodium silicate. Spray-dried sodium silicate particles, as well as other spray-dried silicate particles, are substantially hollow shaped spheres or beads.

The synthetic amorphous silicas are prepared by adding one of the above-mentioned particulate hydrous silicates to an aqueous acid solution. In batch processing, it is preferred that the particulate silicate be added to the acidic solution. In either batch or continuous processing, it is essential that the acid be maintained in excess of the silicate.

It is believed that ion exchange takes place first and polymerization takes place during drying. This reaction occurs as follows:

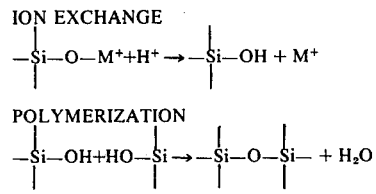

During the ion exchange, essentially no alkali metal silicate dissolves in the liquid phase. This exchange apparently takes place in the solid phase and at the surface of the alkali metal silicate particles.

Any acidic meterial that will serve to exchange hydrogen for the alkali metal ion may be used in the practice of this invention. Examples include: inorganic and organic acids, as well as their acid salts, specifically; sulfuric acid, phosphoric acid, acetic acid, and alkyl sulfonic acids, such as ethane, butane, hexane or decane sulfonic acid and toluene sulfonic acid. Acid salts include: monosodium phosphate, monosodium sulfate, and the like. It is preferred to use sulfuric or phosphoric acid.

The concentration of the acidic solution may vary, but it must be sufficient so that essentially all the alkali metal ions the alkali metal silicate are exchanged for hydrogen ions. For example, in the case of sulfuric acid the initial concentration is from about 1% to about 50% by weight, based on the total weight of the solution, preferably from about 5% to about 20%.

The amount of acidic solution used must be large enough relative to the amount of alkali metal silicate to insure that essentially all alkali metal ions in the solid phase are replaced by hydrogen ions. The use of larger amounts of acidic solution is of no particular advantage and is avoided for reasons of economy. A convenient method for controlling the ratio of acid to silicate is by pH measurement in the reactor. The optimum final pH would depend on the particular choices of raw materials and concentration, but this is easily determined by routine analysis in which the amount of alkali metal ion remaining in the final product is determined. Acceptable final pH values for several choices of raw materials and concentrations can be found in the examples. Such a value for sulfuric acid is from about 3 to about 7.

Adequate reaction time must be provided to allow the exchange of hydrogen ions for alkali metal ions to go substantially to completion. Completion of the reaction can be recognized by observing the cessation of reaction mixture pH drift. This reaction may be carried out at any convenient temperature, for example, from about 15°C. to about 80°C.

Because of the granular nature of the starting alkali metal silicate particles, and because these particles do not appreciably disintegrate during ion exchange, the amorphous silica thus formed can be readily separated from the mother liquor using a filter or centrifuge and washed without difficulty. The silica thus separated does not contain much water and, therefore, requires less drying which is economically advantageous. The amorphous silica formed is dried in any conventional dryer.

Since the particle size of the dried amorphous silica is typically too large (particle diameters vary from below 1 micron to 300 microns) for direct use in dentifrices, it is reduced to a suitable size for dentifrices, for example, by milling. A ceramic ball mill is particularly advantageous. Generally the average particle diameter of the polishing agents of this invention is from about 1 to about 30 microns, preferably from about 3 to about 20. No more than about 1% by weight are larger than 40 microns. The surface area (BET) of the silica polishing agents is from about 100 to about 200 $m^2/gm$. As mentioned, these silica polishing agents have an average refractive index from about 1.410 to 1.440.

As mentioned, as long as the refractive indices of both the solid phase and the liquid phase are essentially identical, a dental cream is translucent. By translucent, it is meant dental creams that are essentially transparent to those that are semi-transparent as exemplified by VASELINE white petroleum jelly. In translucent creams it is preferred that the refractive indices of both the solid and liquid phase be essentially identical.

The solid phase of the translucent dental creams of this invention comprise a polishing amount of the aforementioned synthetic amorphous silica polishing agent. Generally, the solid phase is 5% to about 50% by weight of the dental cream, based on the total weight of the dental cream. Generally, the polishing agent is present in an amount of from about 95 to about 100% by weight, based on the total weight of the solid phase.

The liquid phase comprises water and a humectant. It is 95% to about 50% by weight, based on the total weight of the dental cream. Suitable humectants include: glycerin, sorbitol, other polyhydric alcohols, and mixtures thereof.

The water to humectant ratio is adjusted in the liquid phase such that the refractive index of the liquid phase essentially matches that of the solid phase. In the case of sorbitol, its concentration in the liquid phase is about 47% to about 60% by weight. In the case of glycerin, its concentration is from about 58% to about 75%.

In the opaque dental creams of this invention, the aforementioned synthetic amorphous silica is used as at least part of the cleaning and polishing agent and comprises about 5 to 50% of the total cream. In this case, other conventional polishing agents such as dicalcium phosphate may also be present and it is not necessary to match the refractive index of the liquid phase to that of the silica.

Other ingredients in the liquid phase of either the translucent or opaque creams can be small amounts of flavorings such as oil of winter-green, oil of peppermint, oil of spearmint, oil of sassafras, and oil of anise; and small amounts of sweetening agents such as saccharin, dextrose, levulose, and sodium cyclamate. Still, other ingredients added to the liquid phase include: any of the commonly used foaming or sudsing agents, if they are reasonably stable, non-toxic and foam or form suds within the pH range of the dentifrice of this invention. As examples of suitable sudsing agents, there may be mentioned water soluble alkyl and alkyl ether sulfates and sulfonates having alkyl groups of from about 8 to about 18 carbon atoms, water soluble salts of sulfonates, monoglycerides of fatty acids having from about 10 to about 18 carbon atoms, water-insoluble salts of sulfated fatty alcohols having from about 10 to about 18 carbon atoms, salts of fatty acid amides of taurines such as sodium-N-methyl-N-palmitoyl tauride, salts of fatty acid esters of isethionic acid, and salts of substantially saturated aliphatic acyl amides of saturated aliphatic monoaminocarboxylic acids having from about 2 to about 6 carbon atoms and in which the acyl radical contains from about 12 to about 16 carbon atoms, such as sodium N-lauroyl sarcoside. It is also to be understood that mixtures of two or more sudsing agents can be utilized herein. These sudsing agents are generally used in an amount of from about 0.5% to about 5.0% by weight, based on the weight of the dentifrice composition.

Fluoride ions may also be present in the liquid phase. The fluoride ions can be supplied by any innocuous water soluble fluoride compound which is capable of providing at least 100 ppm of fluoride ions on contact with water. The term fluoride ion includes $F^-$ and complex fluoride ions such as $PO_3F^-$. Additionally, the term "innocuous" means a compound which is not undesirably toxic, highly colored, or otherwise objectionable for use in a dentifrice. Suitable innocuous fluoride compounds include many water soluble inorganic fluoride salts and many complex water soluble fluoride containing salts. Such salts include sodium fluoride, potassium fluoride, ammonium fluoride, indium fluoride, palladium fluoride, ferrous fluoride, lithium fluoride, flurophosphates, e.g., $Na_2PO_3F$, fluorosilicates, e.g. $Na_2SiF_6$ and $H_2SiF_6$, fluorozirconates, e.g., $CaZrF_6$, $Na_2ZrF_6$ and $K_2ZrF_6$, fluoroborates, e.g., $NaBF_4$ and fluorotitanates. Mixtures of the aforementioned fluoride salts can also be used.

Although the above fluoride compounds are all inorganic salts, it is not necessary that such salts be employed as the source of the fluoride ions. Fluoride ions may also be supplied by organic fluorides which are water soluble or at least dissociate to give fluoride ions in contact with water. Fluoride ions can also be supplied by organic hydrofluorides, e.g., amino acid hydrofluorides and amine hydrofluorides, amine fluorides, and mono-, di- and triethanolamine fluorides and hydro fluorides. Examples of suitable organic fluorides of these types are disclosed in Canadian Pat. Nos. 543,066 and 594,533 and in a publication by H. R. Mühlemann et al in Helvetica Odontologica Acta, Vol. 1, No. 2, page 23 (1957).

The quantity of the water-soluble fluoride compounds, which may be used in the dentifrice compositions of this invention, should be an amount equivalent to provide at least 25 parts of fluoride ions per million parts of the total dentifrice composition. It has been found that extremely large amounts of fluoride ions do not appreciably enhance the desirable properties of the dentifrice and may, under certain circumstances, produce toxic effects. Accordingly, it is desirable that the dentifrices of the present invention contain not more than a total of about 4,000 – 5,000 parts of ionized and unionized fluorine per million parts of dentifrice composition and preferably not more than 3,000 ppm. However, a level of from about 1000 to about 10,000 ppm fluoride ions can be used if desired without toxic effects. A preferred level of fluoride ions is from about 500 ppm to about 2,000 per million parts of the total dentifrice composition. Fluoride salts employed in conjunction with the abrasives of this invention may also contain stannous ions for the additional beneficial effects derived from these enamel solubility reducing cations. Examples of suitable stannous compounds are stannous fluoride, mixed halides such as stannous fluorides, and fluorostannates. Stannous tin may also be supplied from soluble stannous compounds other than a fluoride, e.g., stannous chloride or stannous gluconate. Stannous fluoride generally is used in amounts less than 50,000 parts per million by weight, based on the total weight of the dentifrice composition. It is preferred that this salt, i.e., $SnF_2$, level be less than 25,000 ppm and between the range of from about 200 ppm and 2,000 ppm by weight.

In addition to the aforementioned ingredients, it may also be necessary, in order to obtain the proper consistency in certain toothpastes, to add various thickening materials. As examples of such thickening materials there may be mentioned water-soluble salts of cellulose ethers such as sodium carboxymethylcellulose and sodium carboxymethyl hydroxyethyl cellulose. Natural gums such as gum karaya, gum arabic, and gum tragacanth also can be used as thickeners, but may tend to cause undesirable odors or flavors in some formulations. Coloring agents, preservatives, as well as iridescent or pearlescent flakes, may also be used.

All of the aforementioned ingredients which are utilized in the present invention dentifrice compositions, may be incorporated therein in any order, in order to formulate said compositions.

The dentifrices of the present invention may be prepared in any convenient manner, by those skilled in the art. It is preferable to premix the thickener, water and humectant before addition of the synthetic amorphous silica polishing agent of this invention in order to avoid lump formation, after which the remaining ingredients will then be added. The entrapment of air can be prevented by mixing the ingredients under vacuum.

It is desirable that the pH of the dentifrice composition is from about 5 to about 8, preferably from about 6 to about 7.

The following examples illustrate the invention. All parts are by weight unless otherwise specified.

EXAMPLE I

Hydrous sodium silicate (HSS) was prepared by extruding a superheated liquid sodium silicate through an orifice to form a porous string followed by further drying and grinding. The HSS formed has the following composition: $SiO_2$ — 55.6%, $Na_2O$ — 22.2%, ($SiO_2/Na_2O$ ratio—2.5), $H_2O$ — 22.2%.

The above HSS, 50 g., was gradually added into 1.5 liter of 2% $H_2SO_4$ solution and agitation was continued for one hour at room temperature until the pH reached 3.5. The reacted solid was filtered, washed twice with water and dried in an oven at 150°C. The dried solid was ground using a laboratory sample grinder. The product thus produced had an average RI of 1.431 and a composition of 92.5% $SiO_2$, 6.5% LOI. Refractive index was determined by the Beck-line method described in R. M. Allen's "Practical Refractometry by Means of the Microscope", pp. 6–7, 2nd Edition, R. P. Cargelle Labs, Inc., and E. M. Chamot and C. W. Mason, "Handbook Chemical Microscopy", page 315, Vol. I, John Wiley and Sons, Inc., 1958. Cargelle certified refractive index liquids (Fisher Catalog No. 13-946-5) in intervals of 0.004 were used for immersion.

When a sample was suspended in a 57% sorbitol aqueous solution, refractive index 1.431, the mixture was translucent.

EXAMPLE II 50 grams of spray-dried HSS (Philadelphia Quartz GD grade) containing 55% $SiO_2$, 27.5% $Na_2O$, 17.5% water and having an $SiO_2/Na_2O$ ratio of 2, were slowly added with agitation to a vessel containing 2.5 liters of 1.0% aqueous solution of sulfuric acid and reacted over a three hour period at room temperature. During this reaction the pH was 6.8. The solid was very easily filtered through a Buchner filter and digested in 1 liter of water for 1 hour. The solid was filtered and dried in a drying oven at 160°C. for 36 hours.

The resulting silica had an average refractive index between 1.412 and 1.416 and contained: $SiO_2$ — 92.0%, soluble $Na_2O$ — 0.35%, $SO_4$<0.1% and $H_2O$ (800°C. ignition) 6.48%.

EXAMPLE III

Two grams HSS having 18.0% $H_2O$ and $SiO_2/Na_2O$ = 3.2 was slowly added to 20 ml. of 1 molar solution of monosodium orthophosphate under agitation and reacted for 1.5 hours at room temperature. The amorphous silica formed was filtered, washed and dried at 140°C. The silica had an average RI of 1.432 and contained $SiO_2$ — 98.1%, and 0.32% soluble $Na_2O$.

EXAMPLE IV 27.2 kg. of sulfuric acid were added to 154 liters of water in a baffled turbine agitated tank. 88.5 kg. of hydrous sodium silicate (Philadelphia Quartz G grade) containing 61.8% $SiO_2$, 19.2% $Na_2O$, 18.5% water and having an $SiO_2/Na_2O$ ratio of 3.2, was added over a 78 minute period to the sulfuric acid solution at 50°C. At this point, the pH was 4.2. This reaction product was then filtered. Water content of the filter cake was 32.5%. It was then dried and milled.

The resulting silica had an average refractive index of 1.430, an average particle diameter of 21 microns, a bulk density of 0.72, a surface area of 192 $m^2/g$ (BET), and contained 94.8% $SiO_2$, 0.025% extractable $Na_2O$, and 0.12% total $Na_2O$.

EXAMPLE V

A dental cream was prepared containing:

| | |
|---|---|
| Sorbitol – 57% | 64.73% |
| Glycerol | 5.00% |
| CMC | 1.40% anhydrous basis |
| Saccharin | 0.20% |
| METHYL PARASEPT | 0.04% |
| PROPYL PARASEPT | 0.01% |
| Amorphous silica of Example IV | 26.00% anhydrous basis |
| Sodium lauryl sulfate | 1.47% |
| Flavor | 1.15% |
| | 100.00% |

The paste was translucent. The RDA* of the paste was 575.

*Radioactive dentine abrasion - Grabenstetter et al, *Journal of Dental Research*, 37, 1060 (1958).

From a consideration of the above specification, it will be understood that many improvements and modifications in details may be made without departing from the spirit and scope of the invention. It is to be understood, therefore, that the invention is not limited, except as defined by the appended claims, which constitute part of the description of the present invention, and are to be considered as such.

What is claimed is:

1. A translucent dental cream comprising
   1. a solid phase comprising about 95 to 100% by weight, based on the total weight of the solid phase, as a polishing agent a synthetic amorphous silica prepared by exchanging hydrogen for the alkali metal ion of a particulate alkali metal silicate having an $SiO_2/M_2O$ ratio of from about 1.6 to about 3.75 and containing 10 to 25% by weight of water, said polishing agent having an average refractive index of from about 1.410 to 1.440 and an average particle diameter of from about 1 to about 30 microns, and
   2. a liquid phase comprising water and a polyhydric alcohol humectant, the refractive index of said liquid phase being essentially the same as the refractive index of said solid phase.

2. A dental cream according to claim 1 wherein said humectant is selected from the group consisting of sorbitol, glycerin and mixtures thereof.

3. A translucent dental cream comprising
   1. a solid phase consisting essentially of from about 95 to about 100% by weight, based on the total weight of the solid phase of a finely divided synthetic amorphous silica polishing agent prepared by exchanging hydrogen for the alkali metal ion of a particulate alkali metal silicate having an $SiO_2/M_2O$ ratio of from about 1.6 to about 3.75 and containing 10 to 25% by weight of water, said polishing agent having an average refractive index from about 1.420 to 1.435 and an average particle diameter from about 3 to about 20 microns, and
   2. a liquid phase consisting essentially of water and a polyhydric alcohol humectant, the ratio of said humectant in said water being such that the refractive index of said liquid phase essentially matches the refractive index of said solid phase.

4. A dental cream according to claim 3 wherein said humectant is selected from the group consisting of sorbitol, glycerin, and mixtures thereof.

5. A composition according to claim 1 wherein visible nontranslucent solid particles are present.

6. A composition according to claim 1 wherein fluoride is present.

* * * * *